United States Patent [19]

Van der Knaap

[11] Patent Number: Plant 6,740

[45] Date of Patent: Apr. 18, 1989

[54] CHRYSANTHEMUM PLANT NAMED GOLDEN IMPALA

[75] Inventor: Jacques C. M. Van der Knaap, De Lier, Netherlands

[73] Assignee: Fides Beheer B.V., De Lier, Netherlands

[21] Appl. No.: 124,480

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Golden Impala, particularly characterized by its flat capitulum form; single daisy capitulum type; golden yellow ray floret color; diameter across the face of the capitulum of 45–75 mm; excellent growth habit, and its yellow-green to yellow disc florets.

1 Drawing Sheet

1

The present invention comprises a new and distinct cultivar of Chrysanthemum, botanically known as *Chrysanthemum morifolium,* and referred to by the cultivar name Golden Impala.

Golden Impala is a spontaneous mutation of Impala, disclosed in a pending application of applicant. The new cultivar was discovered by applicant in a cultivated bed of plants of the parent cultivar Impala in De Lier, Holland in 1984. The new cultivar was immediately recognized by its intense golden yellow ray floret color, as compared to the light pink ray florets of Impala.

The first act of asexual reproduction of Golden Impala was accomplished when vegetative cuttings were taken after discovery of the mutation in a controlled environment in De Lier, The Netherlands by a technician working under formulations established and supervised by Jacques C. M. Van der Knaap. Horticultural examination of selected units has demonstrated that the combination of characteristics as herein disclosed for Golden Impala are firmly fixed and are retained through successive generations of asexual reproduction.

Golden Impala has not been observed under all possible environmental conditions. The phenotype may vary significantly with variations in environment such as temperature, light intensity, and day length. The following observations, measurements and comparisons describe plants grown in De Lier, The Netherlands under greenhouse conditions which approximate those generally used in commercial practice.

The following traits have been repeatedly observed and are determined to be basic characteristics of Golden Impala, which in combination distinguish this Chrysanthemum as a new and distinct cultivar:

1. Flat capitulum form.
2. Single, daisy capitulum type.
3. Intense golden yellow ray floret color.
4. Diameter across the face of the capitulum is 45–75 mm.
5. Yellow-green (immature) to yellow (mature) disc florets.
6. Excellent vigor and growth habit.

In comparison to the parent cultivar Impala, Golden Impala has a better growth habit, bright golden yellow ray florets, and a somewhat larger flower. The flower type, capitulum form, disc floret color, and flower size of Golden Impala are similar to those same characteristics of Impala.

2

Golden Impala is also similar in many respects except flower color to the cultivars Cream Impala, Pink Impala, Salmon Impala and Apricot Impala, all of which are mutations of Impala and disclosed in pending applications of applicant.

The accompanying photographic drawing shows in side view typical inflorescence and foliage characteristics of Golden Impala, with colors being as true as possible with illustrations of this type.

In the following description, color references are made to The Royal Horticultural Society Colour Chart. The color values were determined between 11:00 a.m. and 12:00 noon in August under natural daylight at De Lier. The Netherlands.

Classification:

*Botanical.—Chrysanthemum morifolium,* Ramat., cv. Golden Impala.

INFLORESCENCE

A. Capitulum:
- *Form.*—Flat.
- *Type.*—Daisy.
- *Diameter across face.*—45–75 mm.

B. Corolla of ray florets:
- *Color* (general tonality from a distance of three meters).—Bright golden yellow.
- *Color* (*upper surface*).—RHS 15A.

C. Corolla of disc florets:
- *Color* (*mature*).—Yellow.
- *Color* (*immature*).—Yellow-green.

D. Reproductive organs:
- *Androecium.*—Present in disc florets; numerous.
- *Gynoecium.*—Present in both disc and ray florets; numerous.

PLANT

A. General appearance:
- *Height.*—90 cm.

B. Foliage:
- *Color* (*upper surface*).—RHS 147A.
- *Shape.*—Long lobed and deeply serrated.

. I claim:

1. A new and distinct Chrysanthemum plant named Golden Impala, as described and illustrated, and parts thereof.

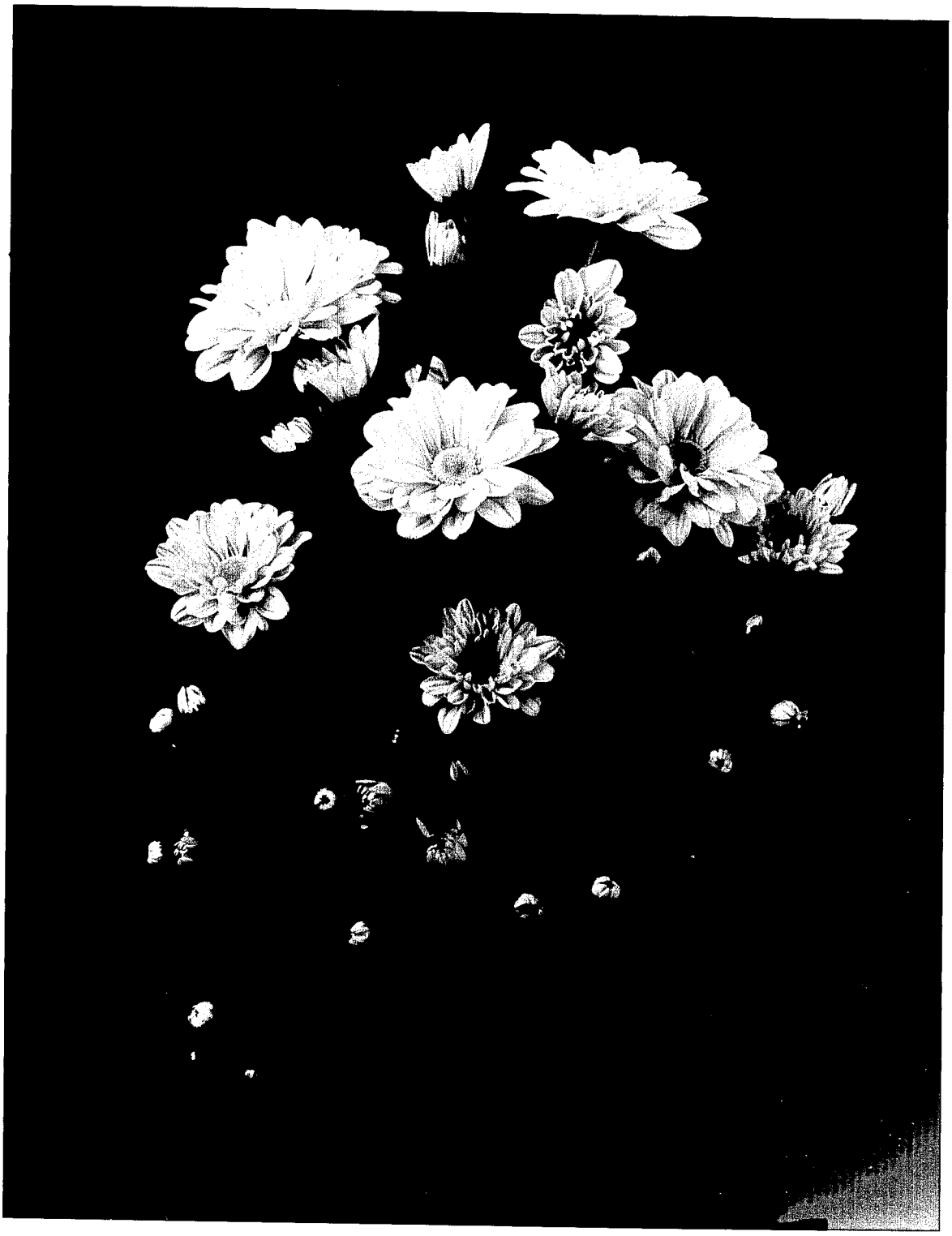

* * * * *